US008834548B2

(12) United States Patent
Liang et al.

(10) Patent No.: US 8,834,548 B2
(45) Date of Patent: Sep. 16, 2014

(54) SYSTEMS AND METHODS TO REGULATE BODY TEMPERATURE

(75) Inventors: Linus Liang, Saratoga, CA (US); Jane Chen, Upland, CA (US); Rahul Panicker, Bangalore (IN); Naganand Murty, Bangalore (IN); Eu-wen Ding, Singapore (SG); Rajan Patel, Casselberry, FL (US)

(73) Assignee: Embrace, San Francisco, CA (US)

( * ) Notice: Subject to any disclaimer, the term of this patent is extended or adjusted under 35 U.S.C. 154(b) by 517 days.

(21) Appl. No.: 13/153,337

(22) Filed: Jun. 3, 2011

(65) Prior Publication Data

US 2012/0305231 A1    Dec. 6, 2012

(51) Int. Cl.
*A61F 7/00*   (2006.01)
*F27D 11/00*   (2006.01)

(52) U.S. Cl.
USPC .......................... 607/114; 607/108; 219/385

(58) Field of Classification Search
USPC ................ 5/603, 655; 607/96–114; 219/385, 219/443.1, 521–526
See application file for complete search history.

(56) References Cited

U.S. PATENT DOCUMENTS

2003/0205568 A1*   11/2003   McConnell et al. .......... 219/386
2010/0010599 A1*    1/2010   Chen et al. .................... 607/112

* cited by examiner

Primary Examiner — Linda Dvorak
Assistant Examiner — Adam Avigan
(74) Attorney, Agent, or Firm — LeClairRyan, a Professional Corporation (57) ABSTRACT

Systems and methods are disclosed for regulating body temperature. The system includes a housing that comprises compartments for a phase change material and a heat transfer material. The compartments are configured to transfer heat from the heat transfer material to the phase change material. A temperature sensor is used to determine when the phase change material has reached a pre-determined temperature. When the pre-determined temperature is reached, a release mechanism or lever is coupled to the temperature sensor to separate the phase change material compartment from the heat transfer material compartment or to remove the heat transfer material away from the phase change material compartment. The heated phase change material compartment can be used to regulate body temperature.

10 Claims, 6 Drawing Sheets

FIG. 5B

SYSTEMS AND METHODS TO REGULATE BODY TEMPERATURE

BACKGROUND

1. Field of Art

The disclosure generally relates to the field of temperature regulation.

2. Description of the Related Art

The human body requires a steady body temperature for proper functioning and health. In extreme temperatures, it can be difficult for the body to sustain a healthy temperature. Illness or other health conditions can also cause the body to lose heat.

In particular, infants must keep a steady body temperature for proper development and overall good health. Premature infants have a low birth weight or conditions that make it difficult for the infant to regulate his or her body temperature. Inability to maintain a proper body temperature can lead to illness or even death of the premature infant. Thousands of low birth weight infants, especially those born to poor families in developing countries, do not have access to incubators or other thermal regulation devices to help regulate their body temperatures.

Conventional systems and methods for regulating body temperature, such as incubators, can be costly and difficult to access for those who cannot afford treatment at hospitals or clinics. Many incubators are bulky, highly technical, and require electricity for operation. Other thermal regulation devices do not effectively regulate temperature and can overheat the body. Over-heating can lead to burning, fever, or other thermal stress-related problems. Accordingly, there is a need to provide safe, effective, and accessible systems and methods for regulating body temperature, especially for infants.

BRIEF DESCRIPTION OF DRAWINGS

The disclosed embodiments have other advantages and features which will be more readily apparent from the detailed description, the appended claims, and the accompanying figures. A brief introduction of the figures is below.

DETAILED DESCRIPTION

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system or method for purposes of illustration only. One skilled in the art will readily recognize from the following description that alternative embodiments of the structures and methods illustrated herein may be employed without departing from the principles described herein.

Configuration Overview

Figure 1A:
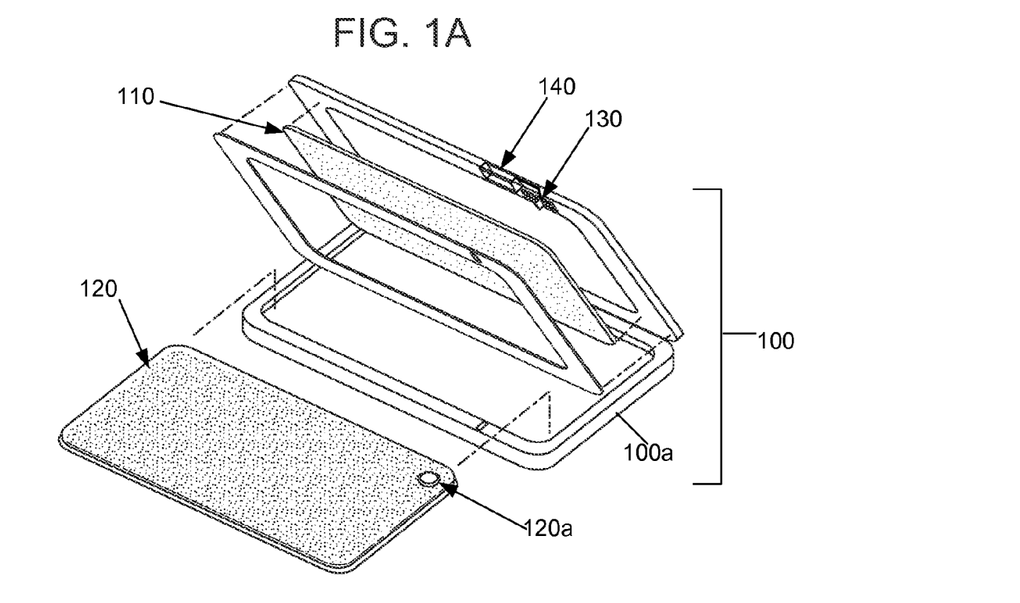
FIG. 1 illustrates one example embodiment of a body temperature regulating apparatus.
Figure 1B:
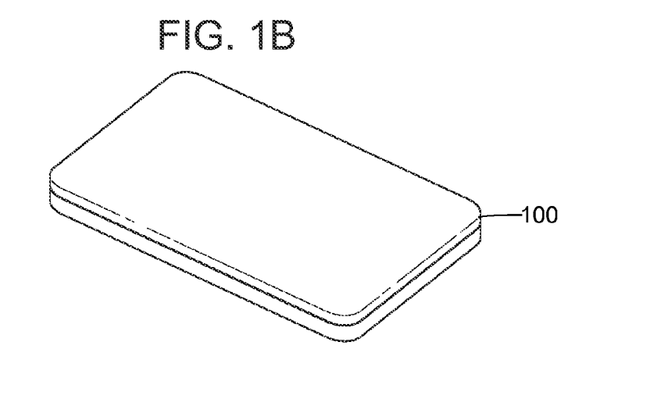
Figure 1C:
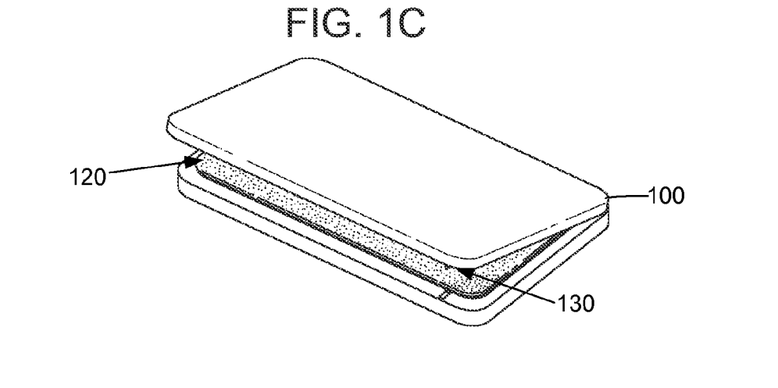

One embodiment of a disclosed system and method for regulating body temperature, for example, the body temperature of an infant, is shown in FIGS. 1A-1C. FIG. 1A illustrates a body temperature regulating apparatus 100. In some embodiments, the body temperature regulating apparatus 100 includes a housing 100a, a phase change material (PCM) compartment 110, a heat transfer material compartment 120, a secure-release mechanism 130, and a temperature sensor 140 coupled with electronics.

The body temperature regulating apparatus 100 can be composed of metal, aluminum, or other heat conducting material that allows transfer of heat through the body temperature regulating apparatus 100. The body temperature regulating apparatus 100 can also be designed in a box or rectangular shape, as shown in FIG. 1A.

The housing 100a can be configured to hold the PCM compartment 110 and the heat transfer material compartment 120. In one embodiment, the housing 100a has a top portion (which can hold the PCM compartment) and a bottom portion (which can hold the heat transfer material compartment). The housing 100a can also be configured such that the PCM compartment 110 and the heat transfer material compartment 120 are positioned on top of each other and/or in direct contact with each other. In certain embodiments, a divider is placed between the PCM compartment 110 and the heat transfer material compartment 120, and heat can transfer through the divider. The housing 100a can be configured to open and close, such that the PCM compartment 110 and/or the heat transfer material compartment 120 can be removed or inserted into the housing 100a. The PCM compartment 110 and the heat transfer material 120 can be made of aluminum, metal, plastic, or other materials that allow for the transfer of heat to the PCM inside the compartment.

The PCM compartment 110 includes the PCM. In some embodiments, the PCM is a material that changes from a first phase to a second phase. For example, the PCM can transition in phase from a solid state to a liquid state when the solid is heated to the appropriate melting temperature. The PCM can be a wax or a wax-like substance. When the temperature of the PCM is below the melting temperature, the PCM is in a solid form. When the temperature of the PCM is above the melting temperature, the PCM is in a liquid form. In some embodiments, the PCM can maintain a constant temperature for an extended period of time (e.g., several hours) at its melting temperature. The PCM has a first phase and a second phase (e.g., a first phase can be a solid or liquid, and the second phase can be a liquid or a gas). In some embodiments, the PCM is a wax or wax-like substance that is formulated in an emulsion (e.g., water and PCM combined to form an emulsion).

In some embodiments, the heat transfer material compartment 120 is designed to contain a liquid, and in particular, a heated liquid. In one embodiment, the liquid is water. In some embodiments, the heat transfer material compartment 120 includes an opening 120a to receive a liquid. The liquid can be heated separately and poured into the heat transfer material compartment 120 through the opening 120a. The liquid can also be poured into the heat transfer material compartment 120, and then the heat transfer material compartment 120 can be heated. In other embodiments, the heat transfer material comprises a gas or a solid. The heat transfer material compartment 120 can be made of aluminum, metal, or other materials that allow the transfer of heat from the heat transfer material.

The PCM compartment 110 and the heat transfer material compartment 120 can have a rectangular, square, or box-like shape that fits within the body temperature regulating apparatus 100. Various other shapes or designs can be used for the body temperature regulating apparatus 100 and the compartments 110, 120 housed within the body temperature regulating apparatus 100.

The body temperature regulating apparatus 100 can include a secure-release mechanism 130 for opening and closing the apparatus 100. The secure-release mechanism 130 comprises a latch, hook, spring, lever, spring-loaded latch, magnets, pressure-filled bladder, or pressure-filled balloon, etc. In some embodiments, the body temperature regulating apparatus 100 includes a temperature sensor 140 coupled with electronics (or circuitry) inside the housing 100a and connected to the secure-release mechanism 130. In other embodiments, the temperature sensor 140 is configured to trigger the secure-release mechanism 130, which opens the body temperature regulating apparatus 100. Details about the temperature sensor 140, electronics, and secure-release mechanism 130 are described herein.

Example Configurations
1. Heat Transfer Material Removal Configuration

In one embodiment, the body temperature regulating apparatus 100 is configured to have an open configuration and a closed configuration. FIG. 1A shows one example of an open configuration. In some embodiments, the body temperature regulating apparatus 100 has a top portion and a bottom portion. The housing 100a can have a hinged edge that connects the top portion and the bottom portion and allows the body temperature regulating apparatus 100 to open without entirely detaching the top and bottom portions.

In certain embodiments, the top portion holds the PCM compartment 110, and the bottom portion holds the heat transfer material compartment 120. FIG. 1A shows an exploded view of the body temperature regulating apparatus 100 with the PCM compartment 100 enclosed within the top portion of the body temperature regulating apparatus 100. In some embodiments, the PCM compartment 110 can be inserted into the body temperature regulating apparatus 100 and then can be removed. In another embodiment, the PCM compartment 110 is encased within and permanently attached to the body temperature regulating apparatus 100. The heat transfer material compartment 120 can be placed in the bottom portion of the body temperature regulating apparatus 100. In one embodiment, the heat transfer material 120 can be removed and re-inserted into the body temperature regulating apparatus 100.

Referring now to FIG. 1B, the closed configuration of the body temperature regulating apparatus 100 is shown. In the closed configuration, the body temperature regulating apparatus 100 contains the PCM compartment 110 and the heat transfer material compartment 120, and the top and bottom portions of the body temperature regulating apparatus 100 are placed on top of each other to close the apparatus 100. In one embodiment, the PCM compartment 110 and the heat transfer material compartment 120 are in direct contact with each other and heat can be transferred from the heat transfer material compartment 120 to the PCM compartment 110. In another embodiment, the PCM compartment 110 and the heat transfer material compartment 120 are placed on top of each other but are separated by a divider. In certain embodiments, the heat transfer material compartment 120 includes an electric heating element inside the compartment. The electric heating element can be an electric coil or other heat conducting material. The electric heating element can be connected to an electrical source (such as an electric outlet), and the heat generated from the electric heating element can be used to heat up the heat transfer material compartment 120.

In some embodiments, the body temperature regulating apparatus 100 is closed by the operation of a secure-release mechanism 130 that holds the top and bottom portions of the body temperature regulating apparatus 100 together. The secure-release mechanism 130 can be a latch, a lock, a hook, a spring-loaded tab or plunger, a pressure-filled balloon, two or more magnets, or various other reversible coupling mechanisms can be used to control the closing and opening of the body temperature regulating apparatus 100.

In some embodiments, the body temperature regulating apparatus 100 comprises a temperature sensor 140. The temperature sensor 140 can also be referred to as a temperature gauge, thermometer, or thermal sensor. In certain embodiments, the temperature sensor 140 comprises a thermistor (a type of resistor whose resistance varies significantly with temperature). The temperature sensor 140 determines the temperature of the PCM compartment 110 and/or the temperature of the PCM within the compartment 110. In one embodiment, the temperature sensor 140 is located inside the housing and adjacent to the PCM compartment 110. In some embodiments, the temperature sensor 140 is coupled to electronics (or circuitry) that triggers the opening of the secure-release mechanism 130 at a pre-determined temperature. In one embodiment, the electronic system can comprise a battery-operated thermal coupler that triggers the release of the secure-release mechanism 130 at the pre-determined temperature. In one embodiment, the temperature sensor 140 determines that the PCM compartment has reached a pre-determined temperature, e.g., at 37° C., and triggers the thermal coupler to open the secure-release mechanism 130. In another embodiment, the temperature sensor comprises a circuit in which a thermocouple is connected to a battery-powered micro-controller. An algorithm is used by the micro-controller to read temperature measurements from the thermocouple, and this activates a solenoid when a desired temperature is reached.

In another embodiment, the secure-release mechanism 130 can be coupled to a thermostatic device that controls the opening and closing of the secure-release mechanism 130. The thermostatic device can extend and shorten in length based on the temperature of the PCM compartment. The thermostatic device can be a cylindrical shape that extends at room temperature and retracts in length at a high temperature (e.g., 37° C.). In one embodiment, the retraction of the thermostatic device triggers the opening of the secure-release mechanism 130. In another embodiment, the thermostatic device extends a small piston outwards when a desired temperature is reached. The piston can then push a spring loaded secure-release mechanism 130 to move the heat transfer material compartment 120 away from the PCM compartment 110.

FIG. 1C illustrates the open configuration of the body temperature regulating apparatus 100 after the PCM compartment has reached the pre-determined temperature and the secure-release mechanism 130 is released. The heat transfer material compartment 120 can be removed from the body temperature regulating apparatus 100. The body temperature regulating apparatus 100, including the heated PCM compartment 110, can be closed and used for heating purposes. The use of the heated PCM compartment 110 and the body temperature regulating apparatus 100 is described in detail in reference to FIGS. 5A-5B.

Figure 2A:
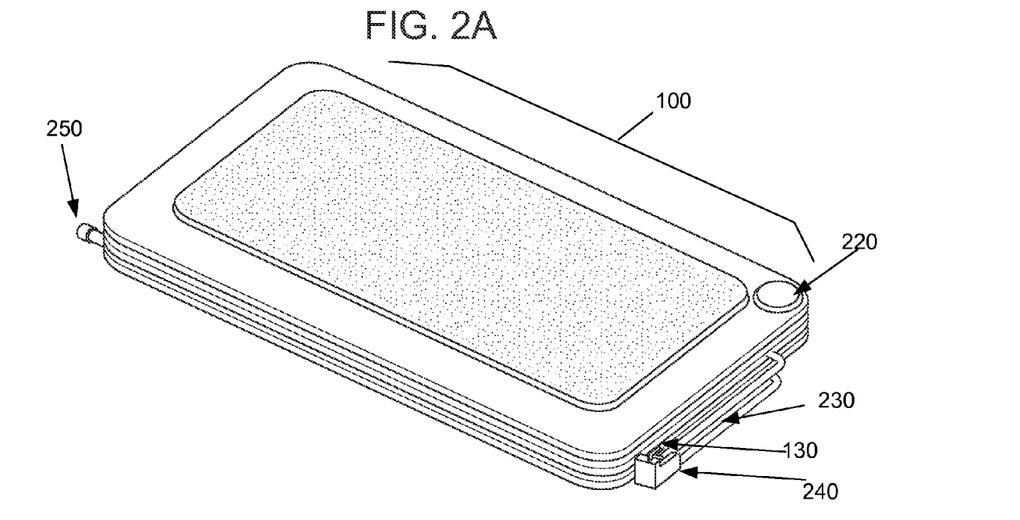
FIGS. 2A through 2C illustrate one example embodiment of the body temperature regulating apparatus.
Figure 2B:
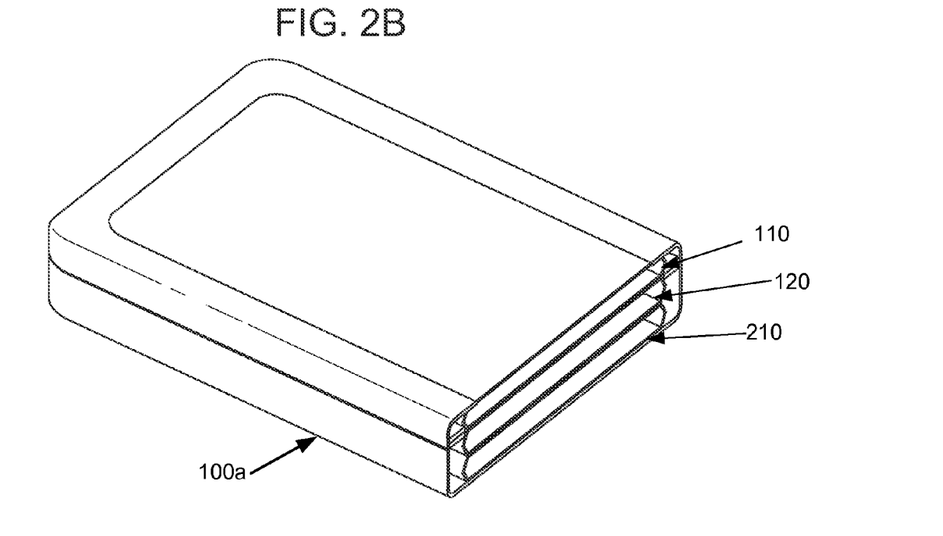

Referring now to FIGS. 2A-2C, illustrated is another example of a configuration of the body temperature regulating apparatus 100. In FIG. 2A, the body temperature regulating apparatus 100 comprises the PCM compartment 110, the heat transfer material compartment 120, and a drain compartment 210. As shown in FIG. 2B, the PCM compartment 110, the heat transfer material compartment 120, and the drain compartment 210 can be stacked on top of each other and enclosed by the housing 100. In one embodiment, the PCM compartment 110 is located on top of the heat transfer material compartment 120, and the two compartments share a common wall. The heat transfer material compartment 120 can be located on top of the drain compartment 210, and the two compartments can share a common wall. In some embodiments, the body temperature regulating apparatus 100 can include electronics, a temperature sensor 140, a secure-release mechanism 130, a drain pipe 230, and a drain pump 240 that connects the heat transfer material compartment 120 and the drain compartment 210.

Figure 2C:
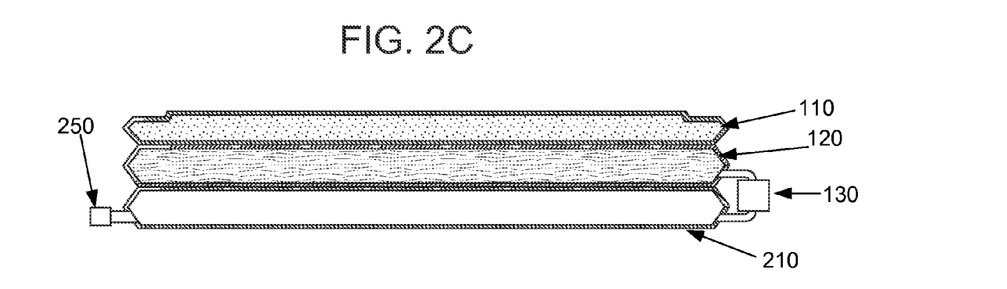

FIG. 2C shows a cross-sectional view of an example of the body temperature regulating apparatus 100. In one embodiment, the heated liquid can be poured directly into the heat transfer material compartment 120 (middle compartment) through an opening 220 in the body temperature regulating apparatus 100. The heated liquid in the heat transfer material compartment 120 can transfer heat to the PCM contained in the PCM compartment 110 based on the contact and/or proximity of the two compartments 110, 120 in the body temperature regulating apparatus 100.

In some embodiments, the heat transfer material compartment 120 is connected to the drain compartment 210 by a drain pipe 220, a tubing, or other type of connection useful for the transport of liquids. In one embodiment, the drain pipe 220 is opened and closed by the secure-release mechanism 130. In certain embodiments, the secure-release mechanism 130 is coupled to a temperature sensor 140 and electronics in the housing of the body temperature regulating apparatus 100. As described herein, the temperature sensor 140 determines the temperature of the PCM compartment 110 and/or the temperature of the PCM within the PCM compartment 110. The temperature sensor 140 signals the electronics to control the opening of the secure-release mechanism 130 at a pre-determined temperature. In one embodiment, the secure-release mechanism 130 of the drain pipe 220 is opened at 37° C.

The drain pump 240 is used to drain the liquid out of the heat transfer material compartment 120. When the secure-release mechanism 130 is opened, the drain pump 240 pumps the liquid out of the heat transfer material compartment 120 through the drain pipe 220 into the drain compartment 210. In some embodiments, the liquid can be removed from the drain compartment 210 through a drain opening 250. After the removal or drainage of the liquid from the heat transfer material compartment 120, the body temperature regulating apparatus 100 containing the heated PCM can be used for heating purposes.

2. Detachable PCM Compartment Configuration

Figure 3A:
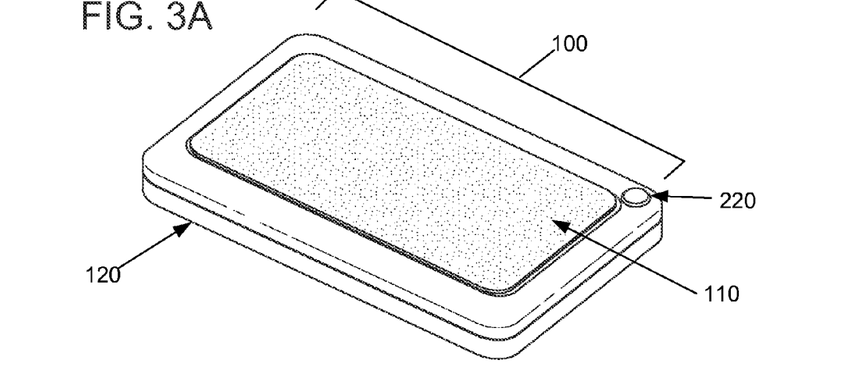
FIGS. 3A through 3D illustrate example embodiments of the body temperature regulating apparatus.
Figure 3B:
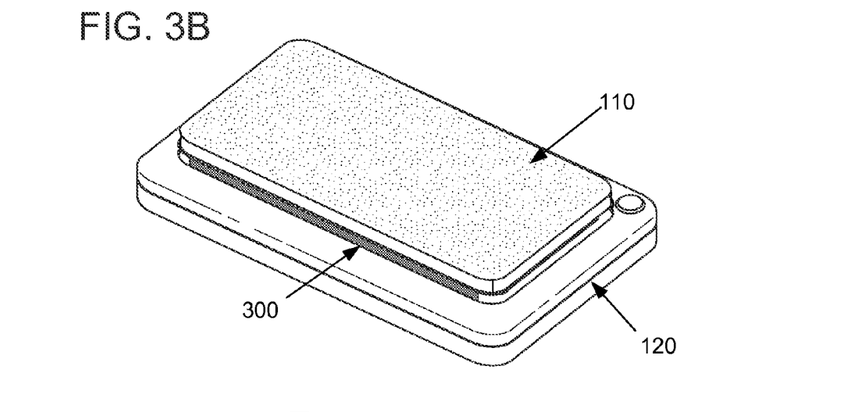
Figure 3C:
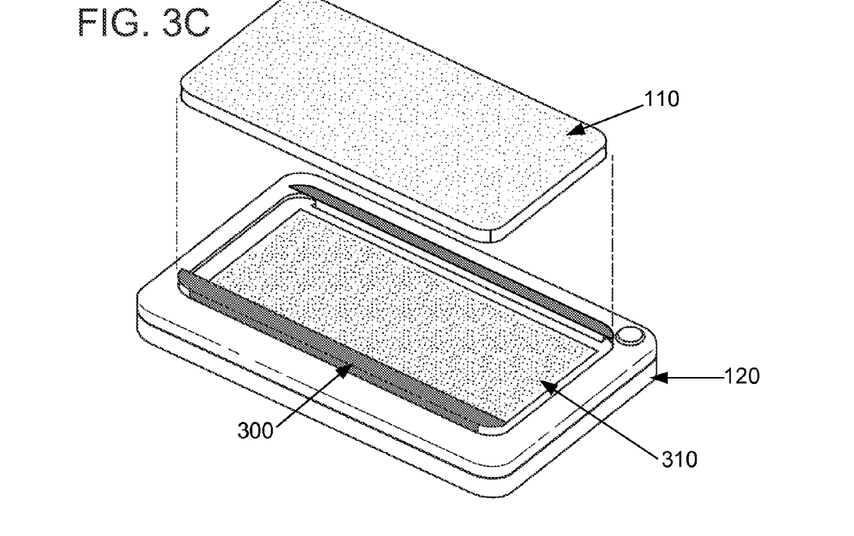

Referring now to FIGS. 3A-3C, illustrated is one example of a configuration of the body temperature regulating apparatus 100. The body temperature regulating apparatus 100 comprises the PCM compartment 110 and the heat transfer material compartment 120. In one embodiment, the heat transfer material compartment 120 is located in a lower portion of the housing and is attached permanently to the housing. The PCM compartment 110 can be configured to be placed directly on top of the heat transfer material compartment 120 and can be detached from the upper portion of the housing. In some embodiments, the PCM compartment 110 and the heat transfer material compartment 120 are in direct contact with each other. In other embodiments, the PCM compartment 110 is placed on a pouch support 310 comprising a flexible membrane that separates the PCM compartment 110 from the heat transfer material compartment 120.

In one embodiment, the body temperature regulating apparatus 100 comprises an opening 220 for pouring a heated liquid into the heat transfer material compartment 120. When the heated liquid is poured into the heat transfer material compartment 120, the heat transfers to the PCM compartment 110 and heats the PCM.

In some embodiments, a temperature sensor 140 in located in the base of the housing and determines the temperature of the PCM compartment 110. In one embodiment, when the PCM compartment 110 reaches a pre-determined temperature, the temperature sensor 140 is coupled to a lever 300 that raises the PCM compartment 110 up and away from the body temperature regulating apparatus 100. For example, when the PCM compartment reaches a pre-determined temperature, e.g., 37° C., the lever 300 is triggered to lift the PCM compartment 110 away from contact with the heat transfer material compartment 120. In another embodiment, a shelf, a panel, or plurality of shelves is coupled to the lever 300 to lift up the PCM compartment 110 from the body temperature regulating apparatus 100. In another embodiment, a spring-loaded apparatus can be coupled with the temperature sensor 140, and the release of the spring can push the PCM compartment 110 away from the heat transfer material compartment 120. As shown in FIG. 3C, the PCM compartment 110 is lifted up from the body temperature regulating apparatus 100 and can be detached for use in heating.

Figure 3D:
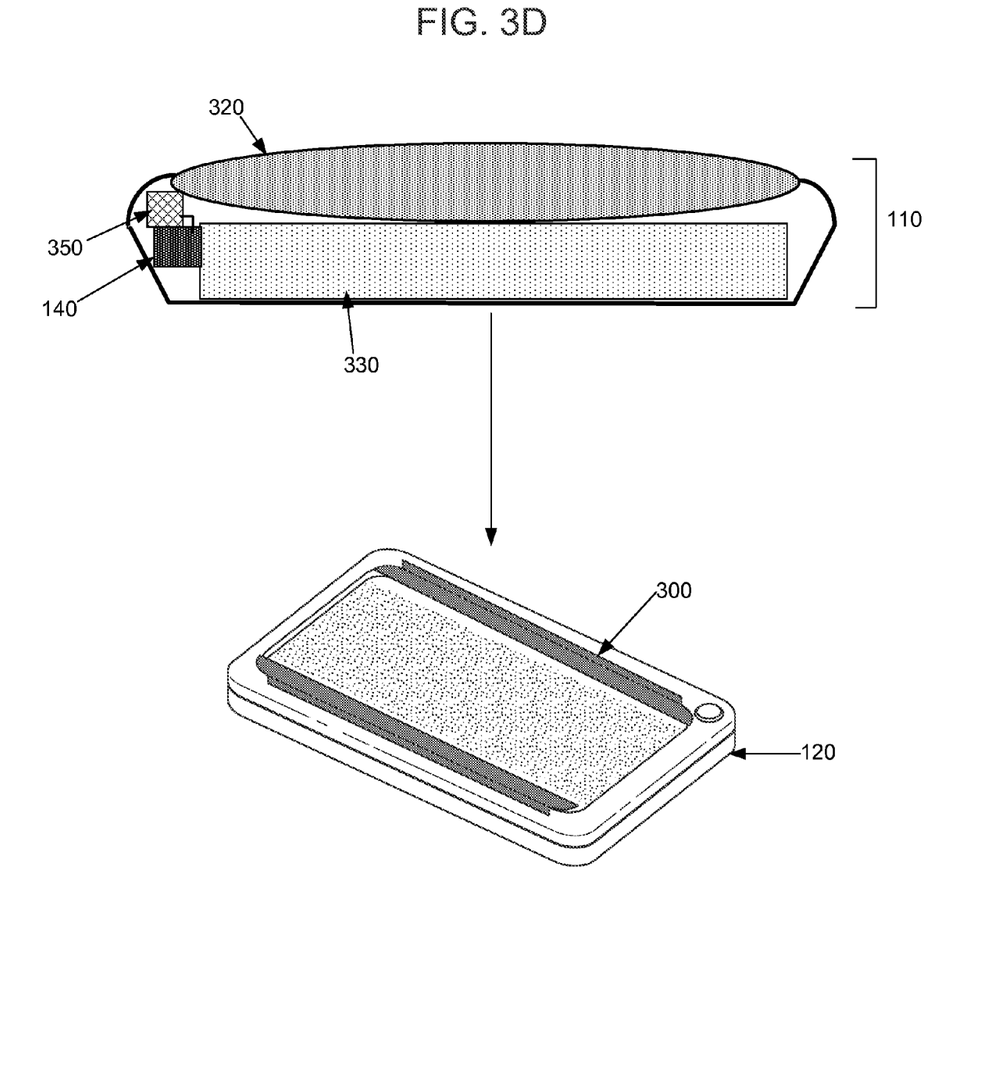

In another embodiment, the PCM compartment 110 itself includes two interior compartments: a top liquid housing 320 and a bottom PCM pouch 330. FIG. 3D illustrates an enlarged, cross-sectional view of the PCM compartment 110 with two interior compartments 320, 330 coupled to electronics 350 and a temperature sensor 140. The PCM compartment 110 is placed on top of the heat transfer material compartment 120.

In one embodiment, the top liquid housing 320 of the PCM compartment 110 can comprise a liquid, such as water, glycerin, or a mixture thereof. The liquid in the top liquid housing 320 helps to distribute the heat evenly from the PCM pouch 330. The top liquid housing 320 also provides a layer of cushion and comfort (e.g., for an infant) when it is placed on top of the PCM compartment 110. The electronics 350 inside the PCM compartment 110 can be coupled with the temperature sensor 140 to determine the temperature of the PCM pouch 330 and/or the top liquid housing 320.

As shown in FIG. 3D, the electronics 350 and the temperature sensor 140 can be located inside the PCM compartment 110. In some embodiments, the electronics 350 and temperature sensor 140 are located solely in the PCM compartment 110 and not located in the heat transfer material compartment 120. In some embodiments, the electronics 350 and temperature sensor 140 within the PCM compartment 110 are coupled to a solenoid (not shown) within the heat transfer material compartment 120. In some embodiments, a solenoid is located within the heat transfer material compartment 120 and has direct contact with or is connected to the temperature sensor 140 and electronics 350 in the PCM compartment 110. When the desired temperature is reached, the temperature sensor 140 and electronics 350 send a signal to the solenoid in the heat transfer material compartment 120 via a circuit connection, and the signal causes the solenoid to activate the lever 300 to lift the PCM compartment 110 away from the lower heat transfer material compartment 120. In some embodiments, as the PCM compartment gets heated, the temperature sensor 140 senses when the top surface of the PCM compartment has reached the desired temperature. When it has done so, the electronics 350 activate the solenoid that is in the heat transfer material compartment 120 so that the lever 300 is released and lifts the PCM compartment 110 up and away from the lower heat transfer material compartment 120, thereby stopping the heat transfer and preventing the PCM compartment 110 from overheating.

3. Gravity Flow Configuration

Figure 4A:
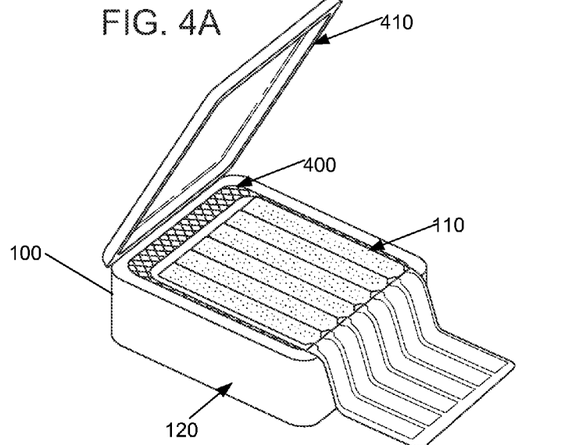
FIGS. 4A through 4C illustrate one example embodiment of the body temperature regulating apparatus.
Figure 4B:
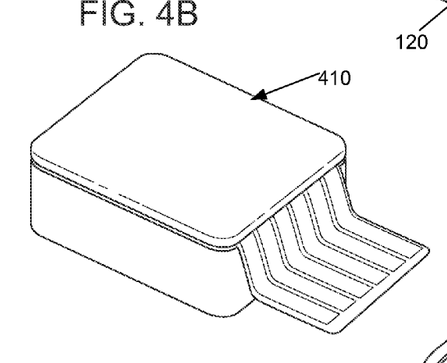
Figure 4C:
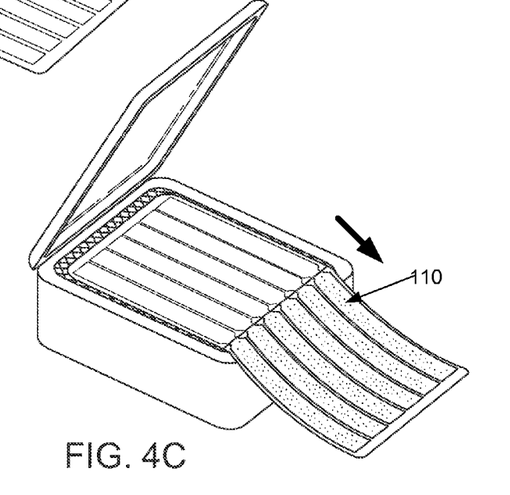

Referring now to FIGS. 4A-4C, illustrated is one example of a configuration of the body temperature regulating apparatus 100. As shown in FIG. 4A, the body temperature regulating apparatus 100 comprises a lower portion, which includes the heat transfer material compartment 120. The top of the heat transfer material compartment 120 comprises a grid-like opening 400, which allows heat from the heated liquid to gravitate upwards.

In some embodiments, the PCM compartment 110 is placed on top of the grid of the heat transfer material compartment 120. The PCM compartment 110 can be a plastic bag, enclosed channel, or other encasement that holds the PCM. In FIG. 4A, the PCM compartment 110 is longer in length than the body temperature regulating apparatus 100. In one embodiment, the PCM compartment 110 has one portion that rests on top of the heat transfer material compartment 120 and another portion that rests on the side or external to the body temperature regulating apparatus 100. The PCM in a solid form is encased on the portion of the PCM compartment 110 that is placed on top of the body temperature regulating apparatus 100. In FIG. 4B, the body temperature regulating apparatus 100 can have a lid 410 or cover that is placed on top of the PCM compartment 110. When the heat from the heat transfer material compartment 120 melts the PCM in the PCM compartment 110, the PCM changes phase, e.g. from a solid into a liquid, and flows by gravity to the lower portion of the PCM compartment 110. As shown in FIG. 4C, when all of the PCM has melted into a liquid form, the lid is lifted, and the PCM compartment 110 can be removed for use for heating purposes.

Example Uses

In some embodiments, the PCM compartment 110 receives heat from a heat transfer material compartment 120, and the heat transfer material compartment 120 can be removed from the body temperature regulating apparatus 100. In other embodiments, the PCM compartment 110 is housed in the body temperature regulating apparatus 100, and the heat transfer material (e.g., liquid) can be drained from the body temperature regulating apparatus 100.

Figure 5A:
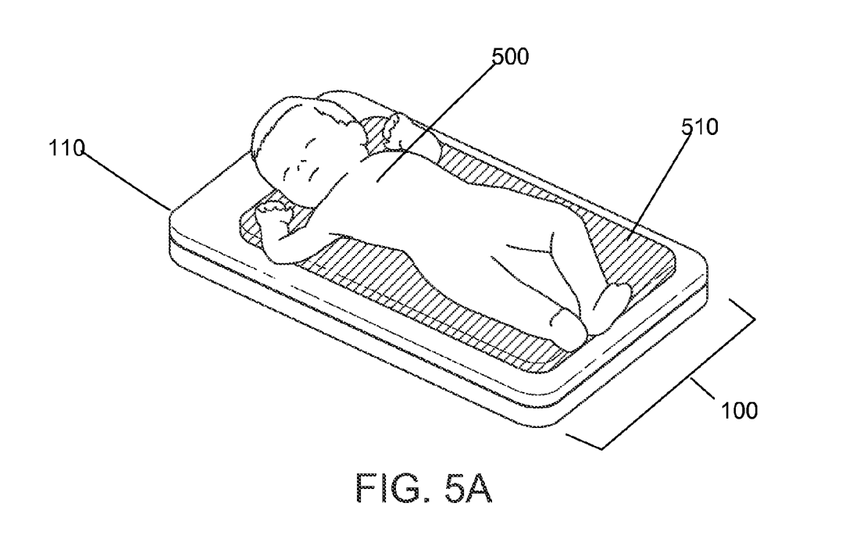
FIGS. 5A and 5B illustrate example embodiments of the use of the body temperature regulating apparatus.

In one embodiment, the body temperature regulating apparatus 100, which includes the heated PCM in the PCM compartment 110, can be used to regulate the temperature of an infant by placing the body temperature regulating apparatus 100 under the infant 500. As shown in FIG. 5A, the infant is warmed by the heat that is emitted by the heated PCM in the body temperature regulating apparatus 100. A sleeping bag 510 (or a covering or a blanket) can be placed between the body temperature regulating apparatus 100 and the infant 500.

Figure 5B:
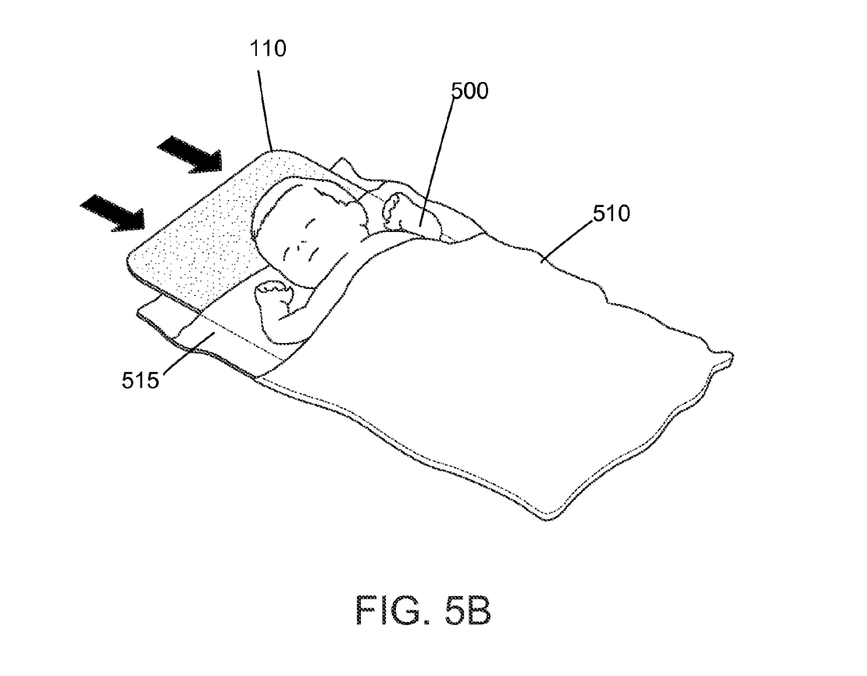

As shown in FIG. 5B, the PCM compartment 110 can be removed from the body temperature regulating apparatus 100 and placed directly into a sleeve 515 (or compartment) of a sleeping bag 510 (or covering or blanket). The infant 500 is placed inside the sleeping bag 510 and is separated from direct contact with the PCM compartment 110 by the sleeve 515. The sleeve 515 can be a layer of cloth or material in the sleeping bag 510. The sleeping bag 510 can be made of cotton, polyester, or other materials that retain the heat of the PCM compartment 110 and can be used to comfortably and safely hold the infant 500. The heat emitted from the PCM compartment 110 helps the infant 500 to maintain a steady body temperature, e.g., 37° C.

The disclosed embodiments beneficially allow for efficient, safe, and cost-effective methods and systems for regulating body temperature. Various other types and designs of body temperature regulating apparatuses 100 can be used to achieve the temperature regulation mechanism described herein. One of skill in the art may alter the compartments 110, 120, 210, temperature sensor 140 and electronics 350, secure-release mechanism 130, and other components without departing from the spirit and scope of the invention.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for regulating the temperature of an infant through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A system for regulating body temperature, the system comprising:
    an enclosable housing comprising a first compartment and a second compartment, wherein the first compartment is adapted to include a phase change material, and wherein the second compartment is adapted to include a heat transfer material, and wherein the first compartment and the second compartment are thermally coupled to transfer heat from the first compartment to the second compartment;

a release mechanism within the housing adapted to reversibly couple the first compartment to the second compartment; and a temperature sensor in the housing, wherein the temperature sensor is adapted to detect a pre-determined temperature of the phase change material and adapted to activate the release mechanism in the housing responsive to detection of the predetermined temperature.

2. The system of claim 1, wherein the first compartment and the second compartment are configured to be in direct contact with each other.

3. The system of claim 1, wherein the release mechanism is configured to release at a predetermined temperature.

4. The system of claim 1, wherein the heat transfer material is a liquid.

5. The system of claim 1, wherein the phase change material is a wax, a wax-like substance, or an emulsion.

6. The system of claim 1, further comprising an opening in the second compartment for receiving the heat transfer material.

7. The system of claim 1, further comprising electronics that are coupled to the temperature sensor and the release mechanism.

8. The system of claim 1, wherein the first compartment includes a phase change material compartment and a heat transfer material compartment.

9. The system of claim 1, wherein the release mechanism is coupled to a lever for moving the first compartment away from the second compartment.

10. The system of claim 1, wherein the release mechanism comprises a secure-release mechanism for decoupling the first compartment from the second compartment.

* * * * *